(12) United States Patent
Fürst et al.

(10) Patent No.: US 6,422,248 B1
(45) Date of Patent: Jul. 23, 2002

(54) DEVICE FOR CLEANING PIPETTE NEEDLES OR STIRRERS

(75) Inventors: Otto Fürst, Viernheim; Thomas Jäck, Schriesheim; Peter Weber, Murnau; Paul Jansen, Mannheim, all of (DE)

(73) Assignee: Roche Diagnostics GmbH, Mannheim (DE)

( * ) Notice: Subject to any disclaimer, the term of this patent is extended or adjusted under 35 U.S.C. 154(b) by 0 days.

(21) Appl. No.: 09/142,261

(22) PCT Filed: Mar. 15, 1997

(86) PCT No.: PCT/EP97/01311
§ 371 (c)(1),
(2), (4) Date: Dec. 15, 1998

(87) PCT Pub. No.: WO97/35173
PCT Pub. Date: Sep. 25, 1997

(30) Foreign Application Priority Data

Mar. 18, 1996 (DE) .......................... 196 10 607

(51) Int. Cl.⁷ ............................ B08B 3/04; B08B 9/02; G01N 35/10
(52) U.S. Cl. ................... 134/22.11; 134/21; 134/22.12; 134/170; 422/100; 436/49; 436/54; 73/864.11; 73/864.22; 73/864.34
(58) Field of Search .......................... 422/63, 67, 100; 436/43, 47, 54; 73/864.11, 864.22, 864.24, 864.34; 134/21, 22.11, 22.12, 170

(56) References Cited

U.S. PATENT DOCUMENTS

| | | | | |
|---|---|---|---|---|
| 3,842,680 A | * | 10/1974 | Vollick et al. | |
| 4,338,280 A | * | 7/1982 | Ambers et al. | 422/68.1 |
| 4,499,053 A | * | 2/1985 | Jones | 422/50 |
| 4,516,437 A | * | 5/1985 | Pedroso et al. | 73/864.22 |
| 4,817,443 A | * | 4/1989 | Champseix et al. | 73/864.22 |
| 4,888,998 A | * | 12/1989 | Buzza et al. | 73/864.21 |
| 5,603,342 A | * | 2/1997 | Shambaugh | 134/154 |
| 5,827,744 A | * | 10/1998 | Fose et al. | 436/49 |
| 6,003,531 A | * | 12/1999 | Kimura et al. | 134/198 |
| 2002/0014255 A1 | * | 2/2002 | Parrish et al. | 134/1 |

* cited by examiner

Primary Examiner—Jill Warden
Assistant Examiner—Kathryn Bex
(74) Attorney, Agent, or Firm—Arent Fox Kintner Plotkin & Kahn, PLLC

(57) ABSTRACT

The invention concerns a device for cleaning pipette needles or stirrers, the device comprising a trough which holds cleaning fluid and whose lower region has a fluid duct for filling and/or emptying purposes and whose upper region has at least one feed pipe which leads into at least one nozzle directed into the trough interior. Advantageously, the device has a cylindrical trough and an insert with nozzles which is screwed into the trough. The invention further concerns a method of cleaning pipette needles or stirrers, the material to be washed being introduced into the trough interior and sprayed with a washing fluid. The device can also be used to flush the interior of a pipette needle.

12 Claims, 9 Drawing Sheets

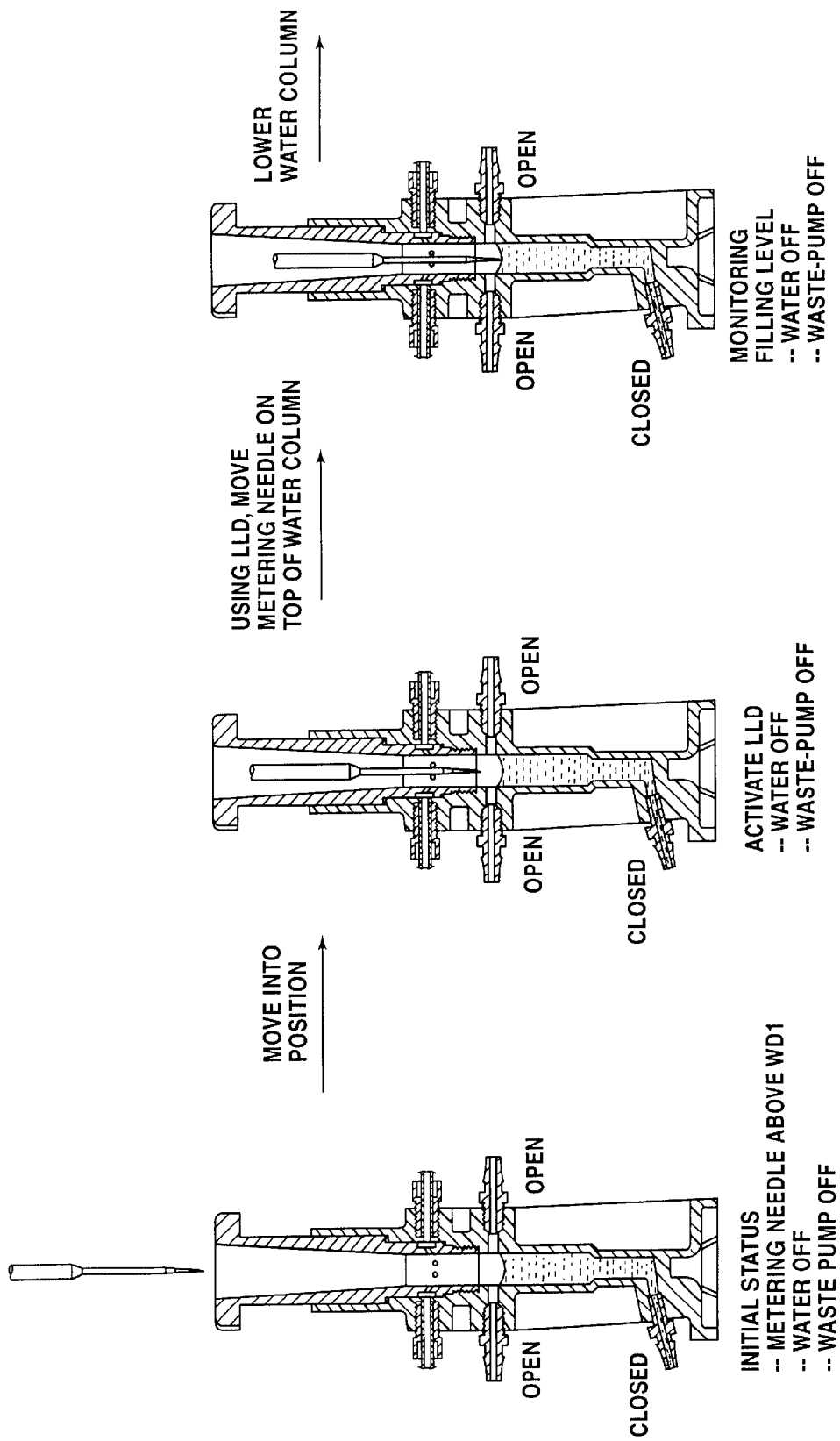

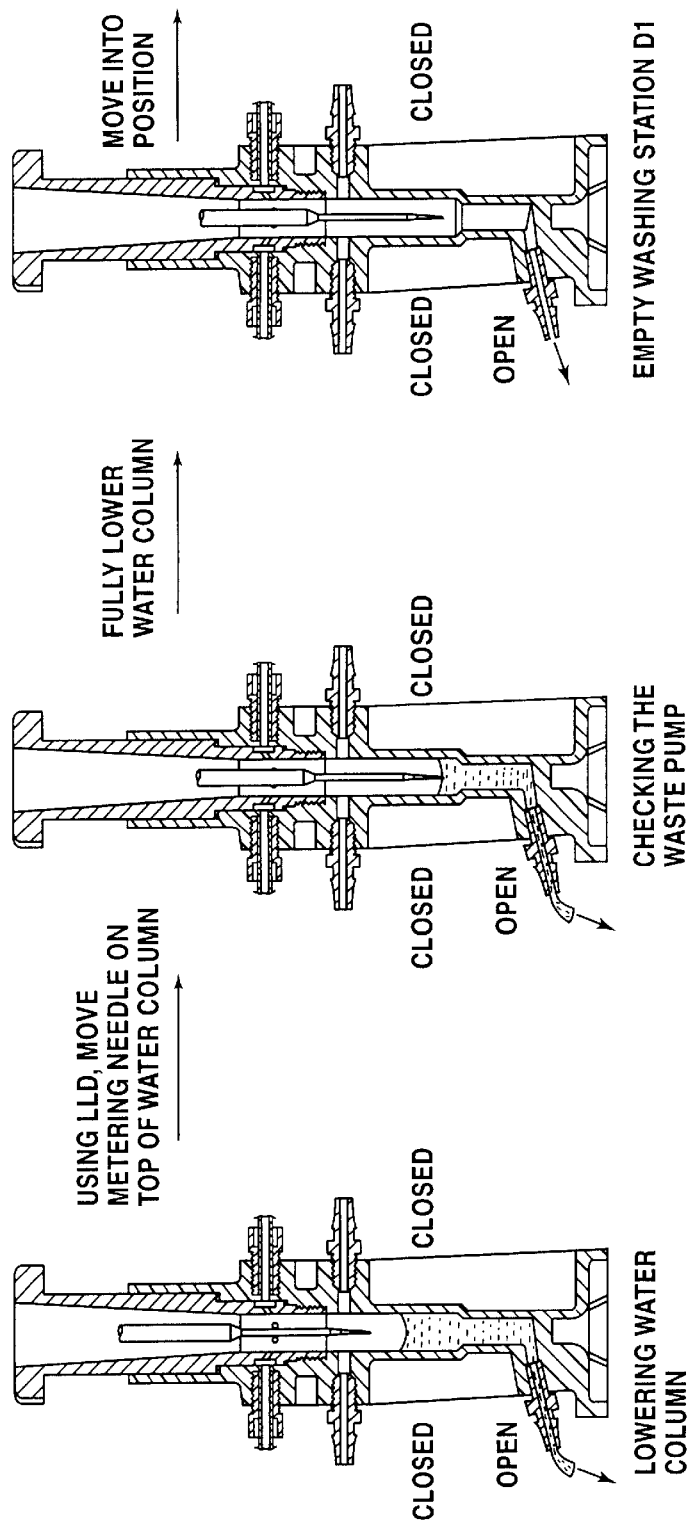

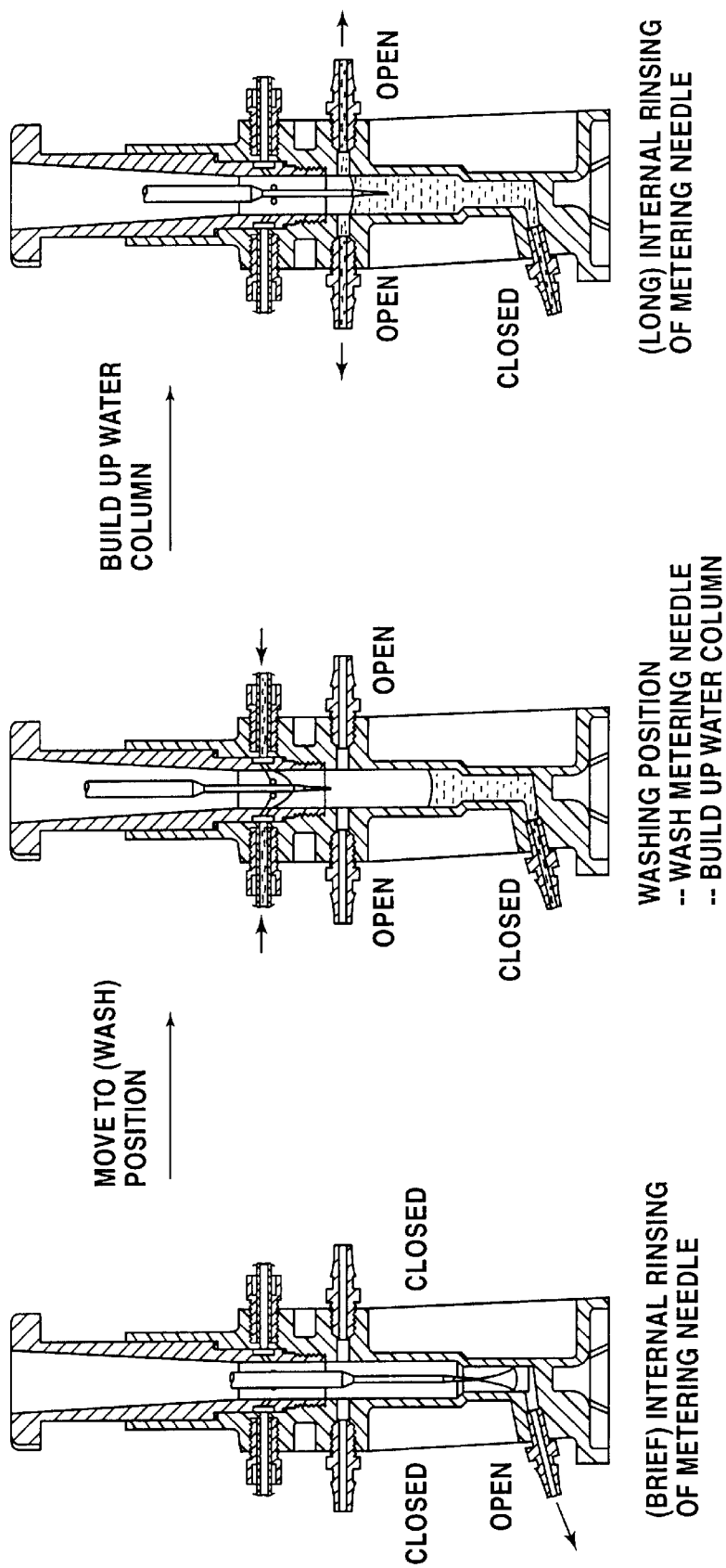

Figure 1:
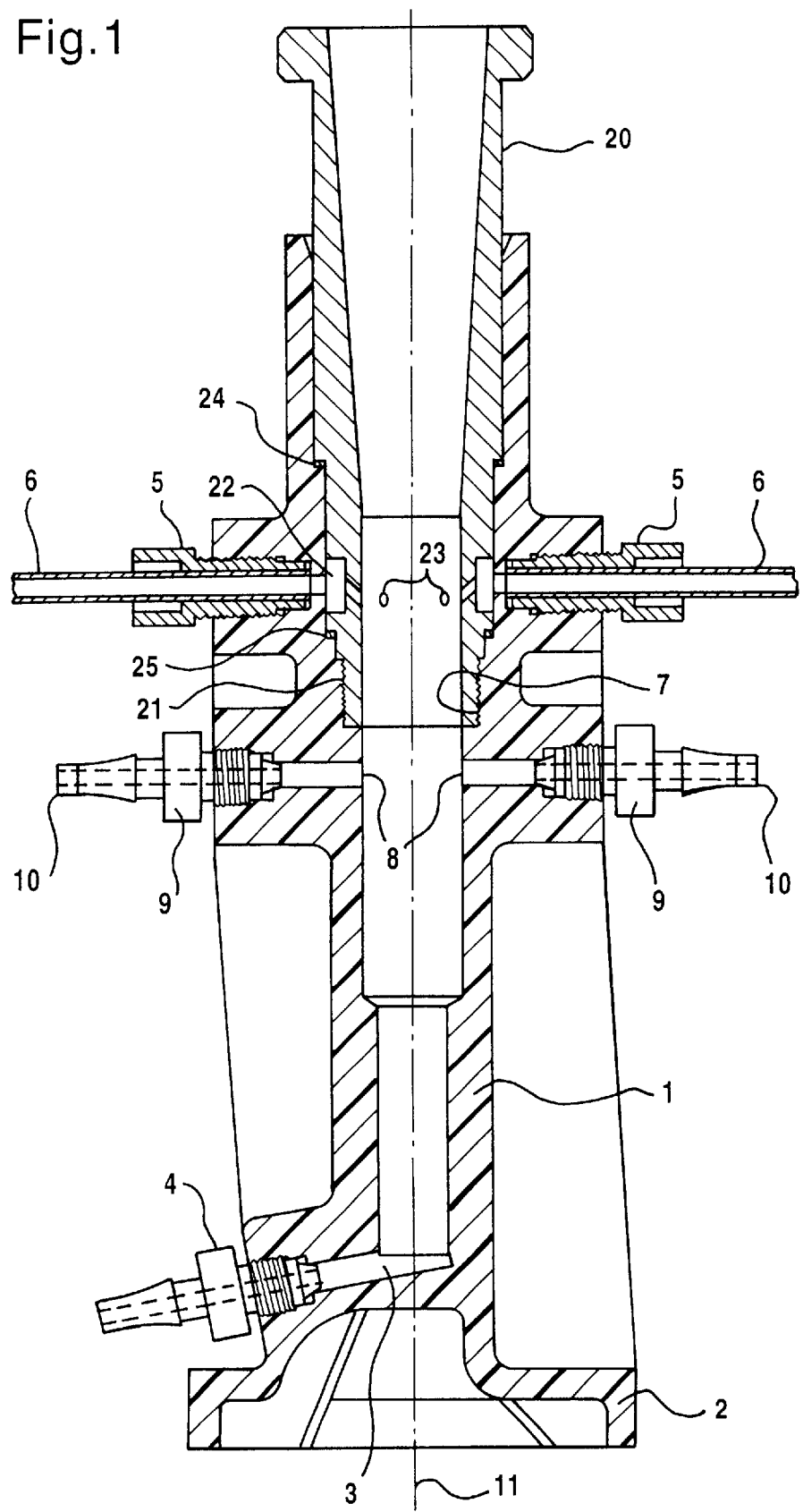

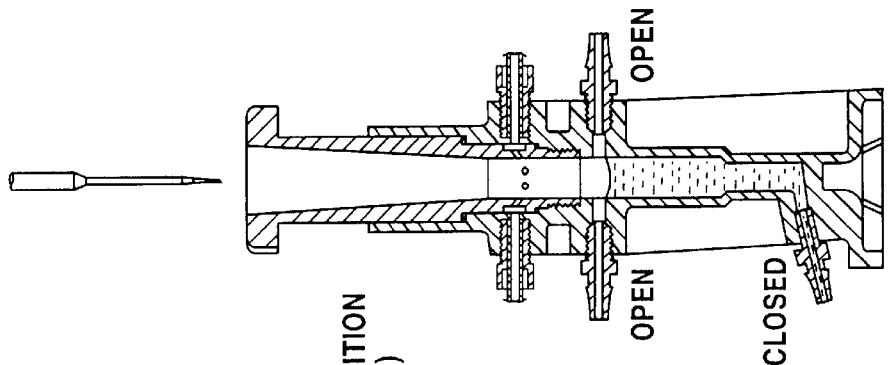
Fig.3(l) INITIAL STATE
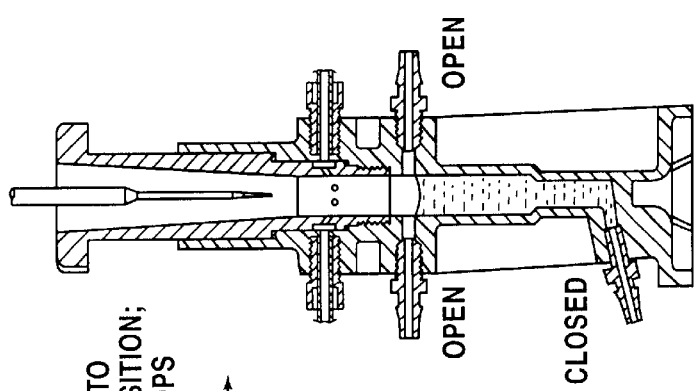
Fig.3(k) REVERSING POSITION
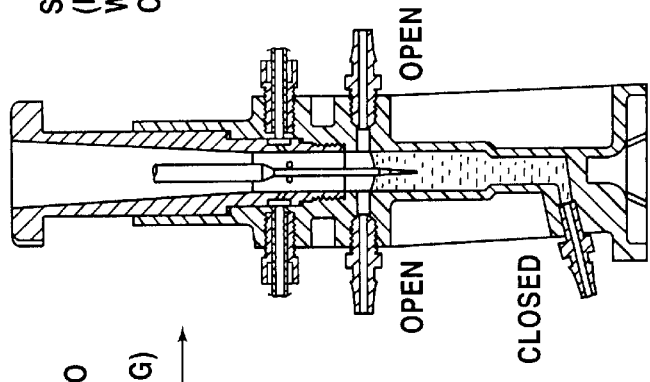
Fig.3(j) WIPING POSITION

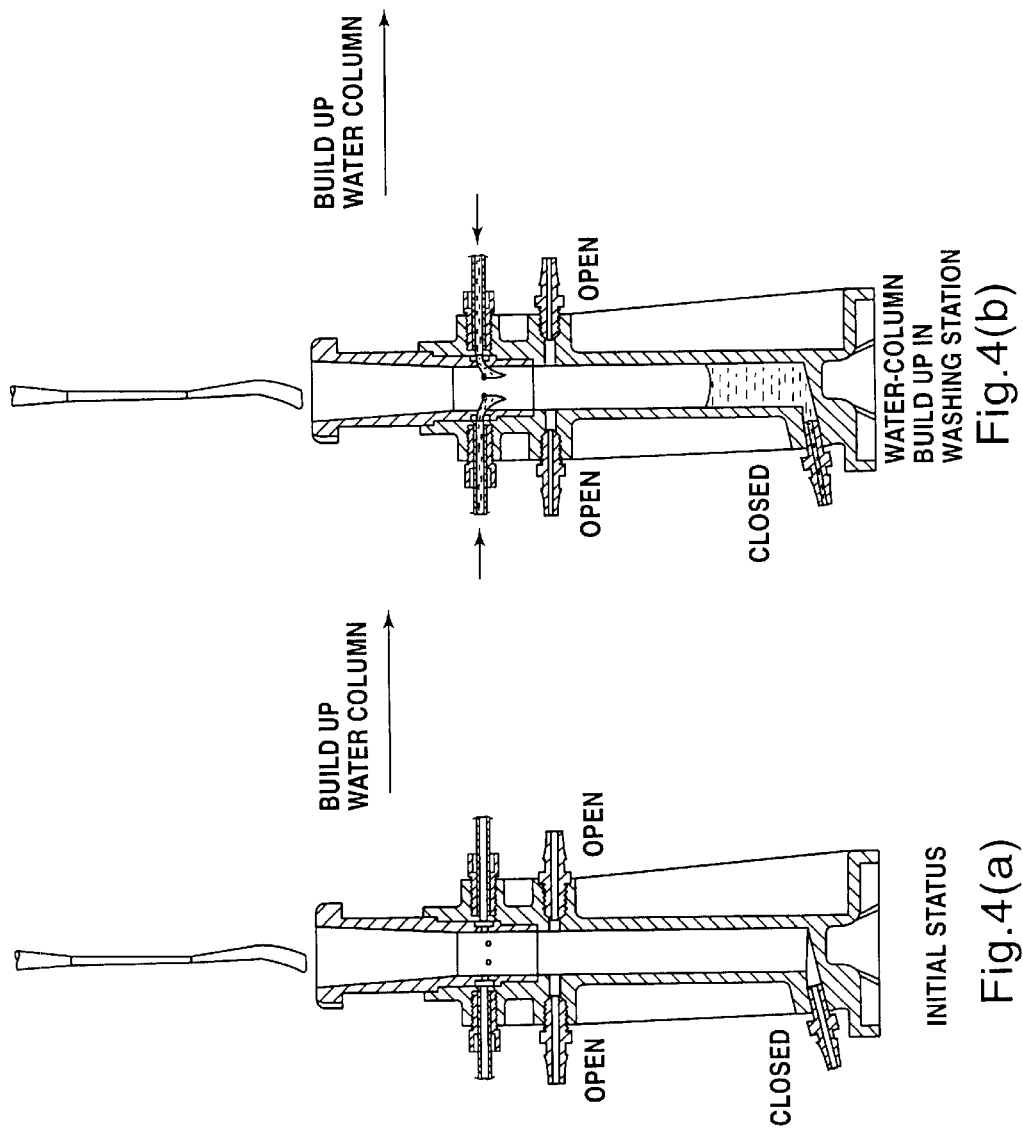

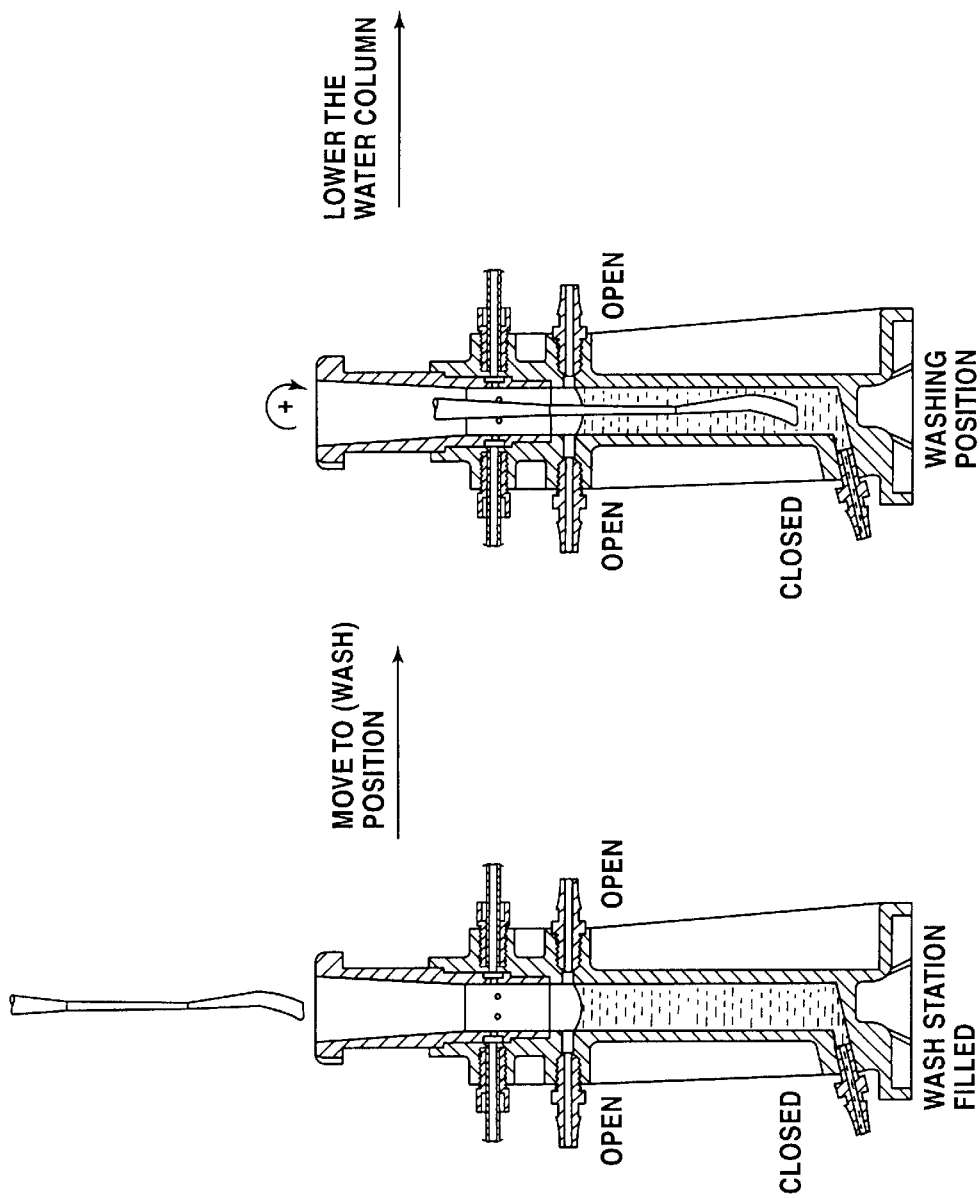

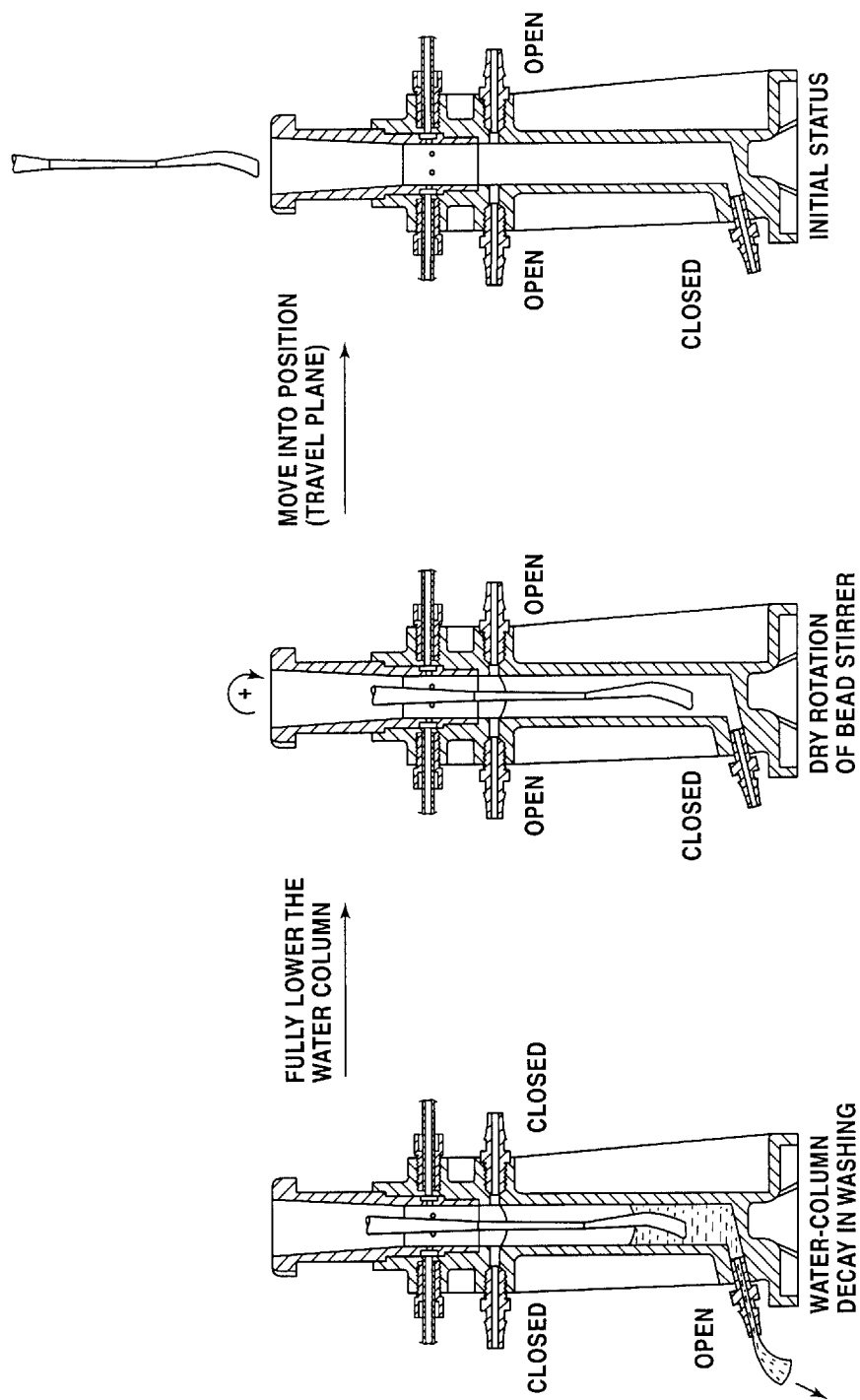

DEVICE FOR CLEANING PIPETTE NEEDLES OR STIRRERS

The present invention is used in the field of automated analysis where liquids are pipetted with pipettes and fluids are stirred with stirrers as necessary.

The present invention provides a device for cleaning pipette probes or stirrers, comprising
- a cavity that holds cleaning fluid and whose lower region has a fluid duct for filling and/or emptying the cavity, and
- at least one inlet tube which empties into at least one nozzle directed toward the interior of the cavity.

When sample fluids such as blood or urine are analyzed, they must be pipetted into containers along with any necessary wash fluids, reagents, etc. The pipette must be rinsed between pipettings to avoid carryover between consecutive samples or reagents. If fluids must be mixed in automated analyzers, this is usually performed using stirrers that are lowered into the sample fluid. The stirrer must be cleaned between each step in the mixing procedure to avoid carryover of the material to be mixed by the stirrer. Examples of materials to be mixed include fluids and suspensions, such as magnetic microparticles in fluid.

Washing device for pipettes and stirrers are known from the prior art in which the devices to be washed are inserted into a cavity filled with wash fluid and the wash fluid is replaced after one or more wash steps. The fluid is usually replaced by removing the fluid through a fluid duct using suction.

A device for washing pipettes is described in European patent application 0 661 542 in which the pipette is inserted into a tube that surrounds the pipette at a distance of 1 mm or less. Fluid is injected into the tube to wash the pipette.

Devices with a cavity known in the prior art have the disadvantage in that the fluid is injected into and emptied from the cavity through the same fluid duct, making it inevitable that used and fresh wash fluid are mixed. Moreover, these devices have the disadvantage that they operate according to a dilution principle. In other words, the fluid that adheres to the pipette is diluted with the wash fluid. Even after the pipette is removed from the cavity, therefore, fluid which is contaminated to a certain extent is still adhered to it. Although this problem is avoided with the device described in EP-A-0 661 542, this device is limited to a certain type of pipette because the duct is designed to accommodate a pipette of a certain diameter. This wash device therefore cannot be used with different types of pipettes or for pipettes and stirrers interchangeably.

The task of the present invention was to provide a device for cleaning pipettes or stirrers very effectively that can be used to clean various objects such as different types of pipettes or stirrers. A further task of the invention was to provide a device with a simple mechanical design that can be integrated into existing automated analyzers or automated analyzer concepts.

A device for cleaning pipettes and stirrers provided by the invention has a cavity for holding cleaning fluid. The cavity is preferably shaped like a hollow cylinder with an internal diameter of between 0.7 and 3.5 cm. The cylinder can also have a base that is not round. The area of the cylinder that is filled with wash fluid is about 10 cm high, although it can vary up or down considerably, depending on the application. The cavity can be manufactured from a number of materials such as metals or plastics, with plastics being the preferred material. The device is preferably designed so that it can be securely attached to a base in an upright position. Moreover, the device has a number of openings.

The lower region of the cavity has an opening that serves as a fluid duct for filling and/or emptying the cavity. This opening is preferably located at the lowest point possible inside the cavity to ensure that used wash fluid can be removed from the cavity as completely as possible. This can be accomplished, for instance, if the bottom of the cavity is bent or slanted.

The upper region of the cavity has one or more openings for fluid ducts that empty into one or more nozzles. The one or more nozzles are directed toward the interior of the cavity and serve to spray a pipette probe or stirrer that is inserted into the cavity. Each of the nozzles is preferably positioned so that the fluid stream ejected from it points downward at a 20 to 70°—and preferably approximately 45°—angle from horizontal. If the device contains numerous nozzles, it is also advantageous for them to be positioned in such a way that the fluid streams meet at one point, preferably in the longitudinal axis of the cavity. In an especially preferred design, the nozzles are located in an insert that can be screwed into the cavity. A groove runs around the outside of the metal insert that contains holes for the nozzles. When the metal insert is screwed into the cavity, an intermediate space forms in the groove between the cavity and the insert that is filled with wash fluid through one or more inlet tubes. In an advantageous design, two inlet tubes are used that are positioned on opposite sides of the cavity. The insert that is screwed into the cavity can be manufactured from a number of materials such as plastics or metals. Metals are preferred, especially stainless steels such as 1.4435 and 1.4305 (old designations: V2A and V4A), that are resistant to cleaning fluids.

It is also advantageous to the function of the device provided by the invention if the upper region of the cavity contains at least one additional opening for another fluid duct, below the nozzles. The cavity can be filled with fresh wash fluid through this fluid duct. This fluid duct can also be used as an outlet for overflowing liquid or to empty fluids using suction to keep the column of water in the cavity at a defined level. This is especially advantageous if the fluid leaving the nozzles cannot be controlled exactly and the fluid level can therefore not be controlled simply by any other means. It is advantageous to know the fluid level in the cavity in advance to eliminate the need to perform liquid level detection, and to avoid inserting the pipette into the fluid farther than desired. This also makes it easier to standardize the wash processes.

The invention also provides a system consisting of a pipette probe attached to a drive arm or a stirrer attached to a drive arm, and a device for cleaning pipette probes or stirrers according to the invention. "Item to be washed" in the context of this application refers to both pipette probes and stirrers. Pipette probes or stirrers attached to a drive arm are commonplace in automated analyzers described in the prior art, so drive arms and their control mechanisms will not be described here in detail. For the present invention, however, it is important that a central control unit be provided that coordinates and regulates the movement of the drive arms and the control of the fluid streams and pumps. The drive arm must move the pipette probe or the stirrer over the opening in the cavity and lower the item to be washed into the cavity. The drive arm must therefore be capable of performing a rotational and translational movement in the vertical planes or translational movements in at least two spacial directions.

The invention also provides a method for cleaning pipette probes or stirrers using a device according to the invention in which the pipette probe or stirrer is inserted into the cavity and sprayed with wash fluid by at least one nozzle. It is favorable to lift the item to be washed to a height at which the area that is wetted with fluid during pipetting or stirring is located entirely below the level of the nozzles. On the other hand, it is unfavorable if an area of the item to be washed is sprayed that is larger than the one described above, because there is a risk of fluid being sprayed on electrical contacts or the like, or of decreasing the effectiveness of the washing procedure. It is especially favorable if the upper edge of the area of the item to be washed described above is located 5 to 5 mm below the level of the nozzle. It is advantageous for the spraying to take place while the item to be washed is lifted out of the cavity. The item to be washed can also be inserted into a wash fluid contained in the cavity. The purpose is to soften any deposits or caked-on substances from the item to be washed and remove them by spraying them with fluid from the nozzles. The item to be washed is cleaned with fresh wash fluid in the spraying step in order to prevent contaminating wash fluid from adhering to the surface of the item to be washed after the cleaning process is over. As a result, the wash station fills with this wash fluid. When cleaning pipette probes, it is also an advantage to rinse the inside of the probes in such a way that the probe is dipped into the wash fluid in the cavity and wash fluid is directed through it. Dipping the pipette probe into the wash fluid prevents the formation of an aerosol and even facilitates cleaning by causing fluid to swirl on the outside of the probe.

It is advantageous for the pipette probe to be dipped into the wash fluid in the cavity and removed at a speed of less than 14 cm/sec to ensure that all fluid covering the probe falls off without forming droplets. Once the pipette probe has left the fluid it can be moved at a higher rate of speed.

The processes for washing a pipette probe described above apply to both the inside and outside of the probe. It is also possible, of course, to wash just the inside or outside of the probe. It is especially advantageous to rinse the outside of the pipette between the individual uptake steps when drawing up two or more different fluids into the same pipette probe in order to prevent or at least reduce carryover. This is especially advantageous when analytical tests are performed with reagents that can also be detected as analytes. In a case like this, the reagent could be carried over from the first test into the sample and then lead to a false-positive test result in a subsequent test of this sample. When drawing up various fluids into one pipette probe, it has proven effective to draw up a separating fluid or a separating air bubble into the pipette probe after drawing up a fluid (e.g., reagent) and only then to draw up another fluid (e.g., reagent or sample).

Wash fluids (also called cleaning fluids) according to the invention refer to the fluids and mixtures commonly used with automated analyzers, e.g., aqueous solutions to which detergents, salts, preservatives, and possibly solubilizers have been added.

A device according to the invention is described in greater detail using the figures below.

FIG. 1: Cross section of a device for cleaning pipette probes/stirrers

Figure 2:
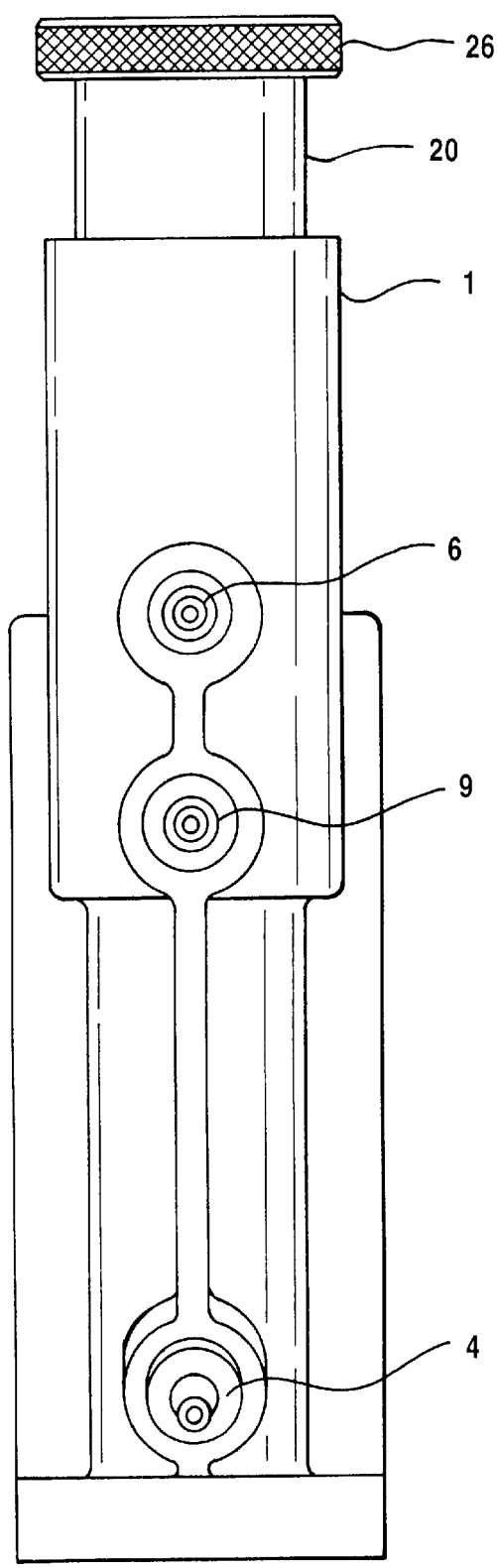

FIG. 2: Outside view of the device

FIGS. 3(a)–(i) Cleaning steps for a pipette probe

FIGS. 4(a)–(g) Cleaning steps for a stirrer

FIG. 1 shows a cross section parallel to the longitudinal axis of the cleaning device according to the invention. The device (1) has a platform (2) on the bottom with which the device can be attached to a ground plate. The device is manufactured via injection molding with PPS (polyphenylene sulfide). The inside of the device is cylindrical in shape and an initial fluid duct enters the device through the bottom of the cylinder. A screw (4) is located on the outside of the device, one end of which is screwed into the device and the other end of which is outfitted with a connection for a tube.

The upper region of the device has two openings on opposite sides of the device into which flanges (5) are screwed. Tubes (6) that carry wash fluid are located inside the flanges (5).

The upper end of the device also has internal threads (7) into which the steel insert (20) is screwed. Accordingly, the insert (20) has external threads (21) in its lower region. A ring-shaped groove (22) is located on the outside of the insert above this thread, and runs all the way around the circumference. Together with the device (1), the groove (22) forms a duct for the wash fluid ejected through the tubes (6). The groove (22) contains holes (23) that serve as nozzles. The device shown in FIG. 1 has six of these holes (23) that are positioned so that the fluid ejected through them meets the cylindrical axis (11) formed by the device. The fluid ejected through the nozzles points downward at a 45° angle from horizontal. The device has two gaskets (24, 25) to seal off the fluid duct located between the device and the insert (20).

The device shown in FIG. 1 also has two openings (8) on opposite sides of the device that are located below the nozzles (23) but above the opening (3). Screws (9) are screwed into these openings and connected to tubes (10). The tubes (10) are connected to a suction device (not shown) to ensure that the fluid level in the cavity does not rise above the level of the openings (8).

FIG. 2 shows a side view of the cleaning device according to the invention. The device (1) and screws (4, 6, and 9) are clearly visible in this drawing. The insert (20) that is screwed into the device projects out of the top of the device. The upper edge of the insert has a flange (26) with a rough-milled surface that facilitates handling when screwing or unscrewing the insert (20). A device according to the invention with an insert screwed into place has the advantage that it is easier to clean when the insert is removed.

FIG. 3 shows the cleaning steps for a pipette probe, also called a dispensing probe. In step (a), the dispensing probe is moved over the cleaning device according to the invention (labelled WD1 in the figure). At this point, fluid from the previous cleaning cycle is already located in the cavity of the cleaning device. In step (b), the pipetting probe (labelled DN) is lowered to the surface of the liquid using electronic liquid level detection (LLD). In step (c), the fill level detected with liquid level detection is checked. The fluid column is then lowered in the cavity (step (d)) and the pipette probe is lowered to the fluid column, which is now lower (step (e)). Using this procedure, the injecting and emptying function of the system can be checked, and the presence of fluid in the cavity can be monitored. The fluid column is lowered completely in step (f) and the pipette probe is lowered into the cleaning device to the point where the probe tip enters a tapered region of the cleaning device (see step (g)). The inside of the pipette probe is now flushed with fresh wash fluid. Since the pipette tip is positioned in the low, tapered region and fluid is removed through the fluid duct on the bottom at this point, the wash fluid exiting the cleaning device is prevented from forming an aerosol, and the upper region of the wash station is prevented from being contaminated with this wash fluid.

After this internal wash step, the pipette is positioned as shown in step (h) so that the pipette tip is washed with the confluence of wash fluid streams. The pipette can be located above or below the surface of the column of wash fluid at this point. The cavity fills with wash fluid when the dispensing probe is sprayed. After washing, the pipette is inserted slightly into the wash fluid (see step (i)). This position can be identical to the position in which fluid falls off of the probe. The interior of the pipette is now rinsed again when fluid is injected through it into the cavity (see step (i)). After this rinse step, the pipette is moved into a defined position in which fluid falls off of the probe (j), if necessary. The pipette is then slowly removed from the wash fluid (step (k)). After the pipette is removed from the cleaning device, it returns to its home position (see step (l)).

If substance to be dispensed is located in the dispensing probe, only the exterior of the probe is rinsed. This cycle begins with the home position (a), skips steps (b) through (g) and continues with (h). The rinsing takes place as described in (h) (the cavity is still filled as shown in (a)). Step (i) is skipped, and the cycle ends with steps (j), (k), and (l). In this procedure, it is advantageous for a small quantity of fluid and/or an air bubble to be drawn up at the end or after step (h). It is especially favorable if fluid is drawn into the dispensing probe from a drop that remains on the tip of the dispensing probe after spraying. It is also possible to draw fluid up immediately from the clean surface of the fluid in the wash station.

An air bubble is drawn up at the end of step (k) or (l). This quantity of fluid, which serves as a separator, is usually less than 5 µl, and is preferably between 1 and 3 µl. The fluid is preferably drawn up only after a reagent drawing up and before a sample drawing up. The same sequence applies for drawing up an air bubble.

FIG. 4 shows the cleaning steps for a stirrer. The home position of the cleaning device with the stirrer is shown in FIG. 4a. A water column is formed and the stirrer is dipped into the wash fluid (FIGS. 4b, c, and d). The stirrer is cleaned by turning it, the column of water is lowered (FIG. 4e). The stirrer is rotated quickly to spin off any fluid still adhering to it (FIG. 4f). The stirrer is then removed from the cleaning device.

LEGEND

1 Device
2 Platform
3 Fluid duct
4 Screw
5 Screw
6 Tube
7 Internal thread
8 Hole
9 Screw
10 Tube
20 Insert
21 External thread
22 Ring-shaped groove
23 Bore holes
24, 25 Gaskets
26 Rough-milled flange

What is claimed is:

1. An apparatus for cleaning automated analysis tools, said apparatus comprising:

a cleaning device including a cavity for passing cleaning fluid therethrough, said cavity including an opening at an upper portion thereof and at least one first fluid duct in a lower portion thereof for filling and/or emptying the cavity;

at least one inlet tube at an upper portion of said cleaning device, said at least one inlet tube being connected to a nozzle which directs fluid toward an interior of the cavity;

at least one outflow channel means for ensuring the fluid within said cavity does not exceed a predetermined level and is located between said at least one first fluid duct and said at least one inlet tube; and a removable cylindrical insert, said cylindrical insert engaging the cavity, wherein one of said cylindrical insert and said cleaning device includes a circumferential groove thereupon, said circumferential groove having a location which corresponds to a location of the at least one inlet tube, thereby forming a channel with an outlet of the inlet tube, wherein said circumferential groove includes a plurality of holes through which the fluid passes to the cavity.

2. An apparatus as recited in claim 1, wherein said bottom of said cavity is defined by an interior bottom of the cleaning device, said bottom being at least partially inclined to direct cavity contents toward said at least one first fluid duct.

3. An apparatus as recited in claim 1, wherein said cavity includes a first cross sectional area at a top, portion thereof and a second cross sectional area at said bottom portion thereof, said first cross sectional area being greater than said second cross sectional area.

4. An apparatus as recited in claim 3, wherein an interior wall of said cavity includes a tapered portion wherein said first cross sectional area of said top portion tapers to said second cross sectional area of said bottom portion.

5. An apparatus as recited in claim 1, wherein the outlet of the inlet tube comprises at least one nozzle directed inwardly toward the cavity.

6. An apparatus as recited in claim 1, wherein said channel is connected to said plurality of holes, each hole of said plurality of holes being directed toward an axial center of the cavity.

7. The apparatus according to claim 1, wherein said cylindrical insert is comprised of metal.

8. The apparatus according to claim 1, wherein said cylindrical insert further comprises at least one nozzle connected to the channel formed by cooperation of said cavity and said cylindrical insert.

9. An apparatus as recited in claim 1, wherein an upper end of the removable cylindrical insert is threaded to facilitate screwing and unscrewing of the removable cylindrical insert into and from the cavity.

10. An apparatus for cleaning automated analysis tools, said apparatus comprising:

a cleaning device including a cavity for passing cleaning fluid therethrough, said cavity including an opening at an upper portion thereof and at least one first fluid duct in a lower portion thereof for filling and/or emptying the cavity;

at least one inlet tube at an upper portion of said cleaning device, said at least one inlet tube being connected to a nozzle which directs fluid toward an interior of the cavity;

at least one outflow channel means for ensuring the fluid within said cavity does not exceed a predetermined level and is located between said at least one first fluid duct and said at least one inlet tube; and a removable cylindrical insert that includes threads which engage threads on the cleaning device so that said cylindrical insert is screwed into the cavity, said cylindrical insert engaging the cavity, wherein one of said cylindrical insert and said cleaning device includes a circumferential groove thereupon, said circumferential groove having a location which corresponds to a location of the at least one inlet tube, thereby forming a channel with an outlet of the inlet tube, wherein said circumferential groove includes a plurality of holes through which the fluid passes to the cavity.

11. An apparatus for cleaning automated analysis tools, said apparatus comprising:

a cleaning device including a cavity for passing cleaning fluid therethrough, said cavity including an opening at an upper portion thereof and at least one first fluid duct in a lower portion thereof for filling and/or emptying the cavity;

at least one inlet tube at an upper portion of said cleaning device, said at least one inlet tube being connected to a nozzle which directs fluid toward an interior of the cavity;

at least one outflow channel means for ensuring the fluid within said cavity does not exceed a predetermined level and is located between said at least one first fluid duct and said at least one inlet tube; and a removable cylindrical insert that projects out of the cavity, said cylindrical insert engaging the cavity, wherein one of said cylindrical insert and said cleaning device includes a circumferential groove thereupon, said circumferential groove having a location which corresponds to a location of the at least one inlet tube, thereby forming a channel with an outlet of the inlet tube, wherein said circumferential groove includes a plurality of holes through which the fluid passes to the cavity.

12. An apparatus for cleaning automated analysis tools, said apparatus comprising:

a cleaning device including a cavity for passing cleaning fluid therethrough, said cavity including an opening at an upper portion thereof and at least one first fluid duct in a lower portion thereof for filling and/or emptying the cavity;

at least one inlet tube at an upper portion of said cleaning device, said at least one inlet tube being connected to a nozzle which directs fluid toward an interior of the cavity;

at least one outflow channel means for ensuring the fluid within said cavity does not exceed a predetermined level and is located between said at least one first fluid duct and said at least one inlet tube; and a removable cylindrical insert that includes threads which engage threads on the cleaning device so that the cylindrical insert is screwed into the cavity and projects out of the cavity, said cylindrical insert engaging the cavity, wherein one of said cylindrical insert and said cleaning device includes a circumferential groove thereupon, said circumferential groove having a location which corresponds to a location of the at least one inlet tube, thereby forming a channel with an outlet of the inlet tube, wherein said circumferential groove includes a plurality of holes through which the fluid passes to the cavity.

* * * * *